United States Patent [19]

Wheeler

[11] Patent Number: 5,342,332
[45] Date of Patent: Aug. 30, 1994

[54] MALE DISPOSABLE INCONTINENCE DEVICE

[76] Inventor: Alton D. Wheeler, 3940 Fox Meadow La., Pasadena, Tex. 77504

[21] Appl. No.: 96,296

[22] Filed: Jul. 26, 1993

[51] Int. Cl.$^5$ .............................................. A61F 5/44
[52] U.S. Cl. ............................ 604/349; 4/144.1
[58] Field of Search ................ 604/349–353, 604/358, 385.1; 128/760, 761; 4/144.1–144.4

[56] References Cited

U.S. PATENT DOCUMENTS

| | | | |
|---|---|---|---|
| 3,200,415 | 8/1965 | Breece, Jr. | 604/352 |
| 3,295,145 | 1/1967 | Ericson | 4/144.3 |
| 3,613,123 | 10/1971 | Langstrom | 4/144.1 |
| 4,103,062 | 7/1978 | Aberson et al. | |
| 4,197,849 | 4/1980 | Bostick | 604/352 |
| 4,217,901 | 8/1980 | Bradstreet et al. | |
| 4,453,938 | 6/1984 | Brendling | 604/349 |
| 4,551,142 | 11/1985 | Kopolow | |
| 4,573,203 | 2/1986 | Pepplatt | |
| 4,690,679 | 9/1987 | Mattingly, III et al. | |
| 4,806,411 | 2/1989 | Mattingly, III et al. | |

FOREIGN PATENT DOCUMENTS 2142243 1/1985 United Kingdom .

Primary Examiner—Randall L. Green
Assistant Examiner—Rob Clarke
Attorney, Agent, or Firm—William W. Haefliger

[57] ABSTRACT

A male, disposable, incontinence device, comprising a generally delta-shaped package, including an outer, flexible sheet forming a protective container, the sheet defining a front wall and a rear wall, there being a penile first slit in the rear wall; and absorbent material in the container to overlie the slit, and to absorb urine leaked within the container via the slit.

8 Claims, 2 Drawing Sheets

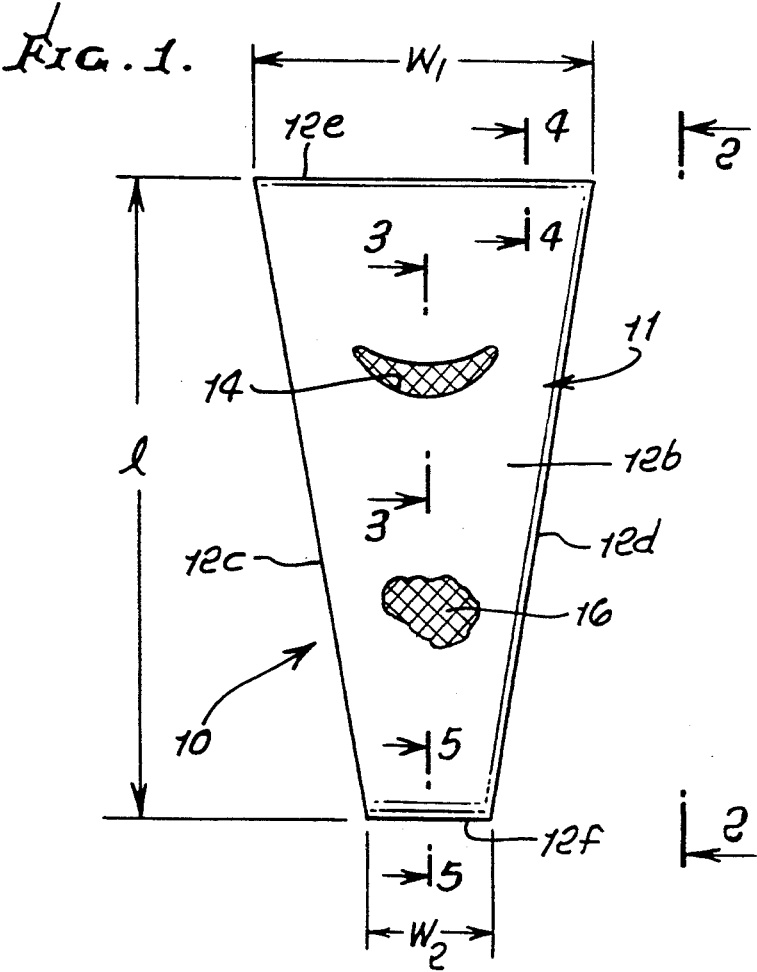
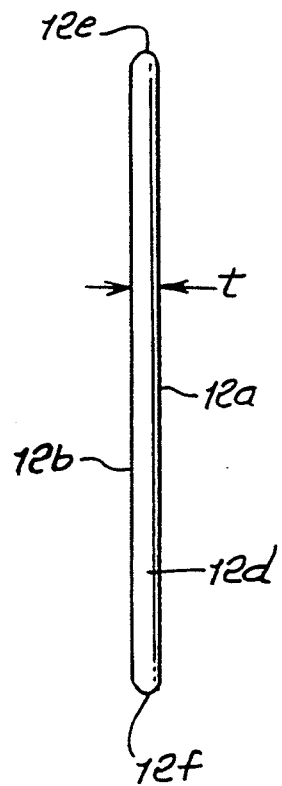
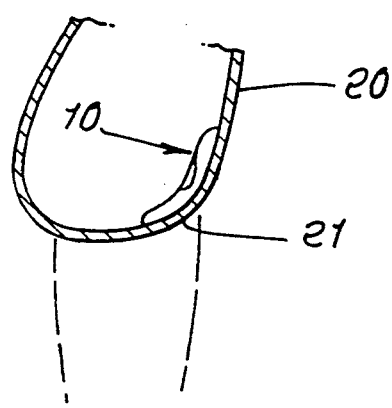

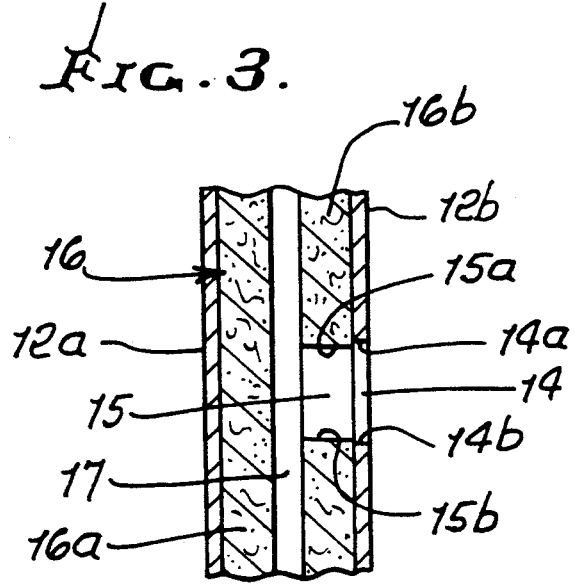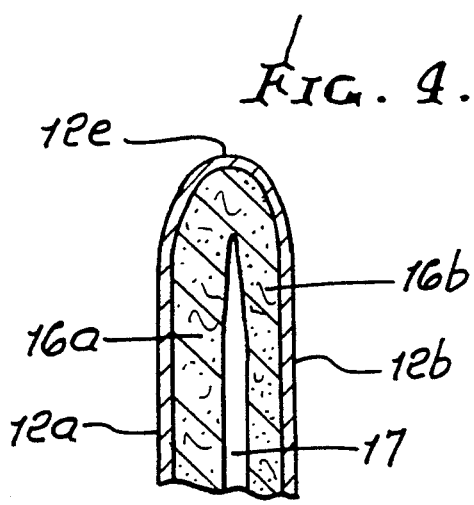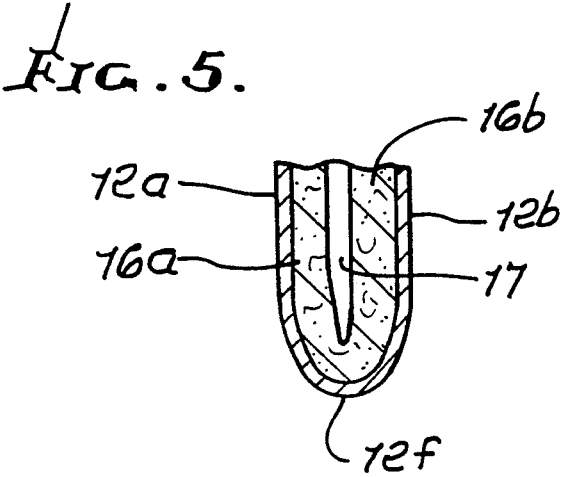

MALE DISPOSABLE INCONTINENCE DEVICE

BACKGROUND OF THE INVENTION

This invention relates generally to incontinence apparatus, and more particularly to male devices of this class.

There is great need for simple, effective, easy to apply and use incontinence devices for males, and which are wearable, reliable and portable. So far as I am aware, there is no prior device which incorporates the unusual improvements and combination of features of construction and use, as well as results, as one now afforded by the present device.

SUMMARY OF THE INVENTION

It is a major object of the invention to provide an improved device meeting the above needs and incorporating the unusual features, as referred to.

Basically, the device comprises, in combination:

a) a generally delta-shaped package, including an outer, flexible sheet forming a protective container, the sheet defining a front wall and a rear wall, there being a penile first slit in the rear wall, b) and absorbent material in the container to overlie the slit, and to absorb urine leaked within the container via the slit.

As will be seen, the absorbent material typically substantially fills the container from a closed relatively narrow lower portion thereof to a divergent upper portion thereof; and the absorbent material may have approximately the consistency of cotton. The outer shell typically consists of thin waterproof paper.

The device is typically worn in body shorts to closely hug the body, and is thus well supported, easily inserted, and easily removed, as needed. The slit typically forms a crescent-shaped gap, as will be seen.

A further object is to provide the absorbent material in the shape of a pouch, with a second penile slit or gap formed in the pouch front wall, and in registration with the first slit.

These and other objects and advantages of the invention, as well as the details of an illustrative embodiment, will be more fully understood from the following specification and drawings, in which:

DRAWING DESCRIPTION

FIG. 1 is a front view of a device incorporating the invention;

FIG. 2 is an edge view of the FIG. 1 device taken on lines 2—2 of FIG. 1;

FIG. 3 is an enlarged fragmentary section taken on lines 3—3 of FIG. 1;

FIG. 4 is an enlarged fragmentary section taken on lines 4—4 of FIG. 1;

FIG. 5 is an enlarged fragmentary section taken on lines 5—5 of FIG. 1; and

FIG. 6 is a section showing the device of the invention, as worn in body shorts.

DETAILED DESCRIPTION

In the drawings, the male, disposable, incontinence device 10, as shown, includes a generally delta-shaped package 11. The latter includes an outer, flexible sheet 12 having spaced, parallel front and back walls 12a and 12b, left and right edges 12x and 12d that taper downwardly, and top and bottom horizontal edges 12e and 12f. The sheet 12 forms a flexible container, and may advantageously consist of thin, lightweight, waterproof paper. Water absorbent material 16 is received in the container to overlie a slit (or slot) 14 formed in rear wall 12a, and in quantity to absorb urine leaked (for example inadvertently) within the container.

The material 16 may itself form a slit or slot 15 (see FIG. 3), in registration with slit 14, the slit 15 being formed in a rear wall 16b formed by pouch 16 of said absorbent material. The pouch front wall appears at 16a. The slits 14 and 15 are penile entry slits; and the pouch space 17 is a penile receptacle space. Both slits may be U or crescent-shaped, and be downwardly convex, i.e., upper and lower edges of the slits at 14a and 14b, and 15a and 15b, may be spaced apart and downwardly convex.

The absorbent material substantially fills the container from its closed lower, narrowed end portion to the divergent upper portion, above the level of slits, whereby its urine absorbency is optimized. The absorbent material may have the soft, compressible consistency of cotton and be fibrous; and another usable absorbent material comprises a thin sponge. The dimensions of the package are typically about as follows for optimum results:

length "1" = $6\frac{1}{2}$ inches
upper width $w_1 = 3\frac{1}{2}$ inches
lower width $w_2 = 1\frac{1}{4}$ inches
thickness $t = 3/16$ to $\frac{3}{8}$ inch.

FIG. 6 shows the package 10 fitted into shorts 20 adjacent and above frontal crotch portion 21 thereof, to be easily insertible in, worn, held in place, and removed from the shorts, whenever desired.

Typical materials for the absorbent material or pouch are: rayon, wood pulp, cotton, polyethylene or polyester fibers and mixtures thereof; see also material as disclosed in U.S. Pat. No. 4,551,142, or in U.S. Pat. No. 4,103,062. The material may be flocced.

I claim:

1. In a male, disposable, incontinence device, the combination comprising:

a) a generally delta-shaped package, including an outer, flexible sheet forming a protective container, said sheet defining a front wall and a rear wall, there being a penile first slit in said rear wall, b) and absorbent material in said container to overlie said slit, and to absorb urine leaked within the container via said slit, c) said absorbent material forming a pouch having front and rear walls, and including a second penile slit in said rear wall and in registration with said first slit, d) said slits having U-shape and being convex downwardly toward the closed lower end of the package, e) said slits having top and bottom edges with a gap therebetween, said gap having crescent shape.

2. The combination of claim 1 wherein said absorbent material substantially fills said container from a closed relatively narrow lower portion thereof to a divergent upper portion thereof.

3. The combination of claim 1 wherein said absorbent material has approximately the consistency of cotton.

4. The combination of claim 1 wherein said outer sheet consists of waterproof paper.

5. The combination of claim 1 wherein said absorbent material includes a water absorbent sponge.

6. The combination of claim 1 including body shorts in which said device is supported.

7. The combination of claim 1 wherein the package has top edge width $w_1$, bottom edge width $w_2$ and length 1 between said top and bottom edges, as follows:

$w_1$ 3½ inches
$w_2$ 1¼ inches
1 6½ inches

8. The combination of claim 1 wherein said slit top and bottom edges are downwardly convex and crescent shaped, said gap between the slits narrowing toward opposite ends of the gap that project upwardly.

* * * * *